United States Patent [19]

Bookwalter et al.

[11] Patent Number: 5,320,444
[45] Date of Patent: Jun. 14, 1994

[54] ENCLOSED SURGICAL APPARATUS CLAMP

[76] Inventors: John R. Bookwalter, 9 Belmont Ave., Brattleboro, Vt. 05301; William H. Bookwalter, 337 College St., Burlington, Vt. 05401

[21] Appl. No.: 7,910

[22] Filed: Jan. 22, 1993

[51] Int. Cl.$^5$ ............................. A61F 5/04; B25B 5/16
[52] U.S. Cl. .................... 403/323; 403/191; 403/DIG. 9; 606/151; 248/231.4
[58] Field of Search ............ 403/191, 192, 199, 200, 403/110, 323, 259, DIG. 9, 390; 606/151; 248/231.4

[56] References Cited

U.S. PATENT DOCUMENTS

| | | | |
|---|---|---|---|
| Re. 17,880 | 11/1930 | Stoeltzlen | 403/191 X |
| 947,811 | 2/1910 | Glidden | 403/191 |
| 1,077,051 | 10/1913 | Dodds | 403/200 X |
| 2,046,942 | 7/1936 | Goeller | 403/191 X |
| 2,699,190 | 1/1955 | Packer | 403/323 X |
| 4,135,505 | 1/1979 | Day | 403/110 X |
| 4,322,087 | 3/1982 | Addicks | 403/191 X |
| 4,546,949 | 10/1985 | Millett et al. | 403/191 X |
| 4,684,286 | 8/1987 | Itagaki | 403/192 X |

FOREIGN PATENT DOCUMENTS 0342878 11/1989 European Pat. Off. ...... 403/DIG. 9
2117822 10/1983 United Kingdom ......... 403/DIG. 9

Primary Examiner—Randolph A. Reese
Assistant Examiner—Christopher J. Novosad
Attorney, Agent, or Firm—Donald W. Meeker

[57] ABSTRACT

A threaded rod has a ball at one end and a stationary jaw at an opposite end with an end cap covering the end of the rod. A threaded collar pushes a movable jaw along the threaded rod toward the stationary gripping jaw by turning the collar clockwise. The movable collar has a cylindrical dome which covers the threaded rod and the end cap. An interior sleeve secured to the threaded collar at one end by an interior ring has a ridge at the other end of the interior sleeve which pulls the movable jaw away from the stationary jaw by turning the collar counter-clockwise to release the jaws. The ball on one end of the clamp is inserted in an existing float and lock ball system attached to a stabilizing post on an operating table bed. The clamp secures surgical apparatus in place over the patient on the operating table.

9 Claims, 1 Drawing Sheet

ENCLOSED SURGICAL APPARATUS CLAMP

BACKGROUND OF THE INVENTION

1. Technical Field

This invention relates to holders for positioning instruments and tools in an adjusted position, and in particular to an enclosed clamp for surgical apparatus, such as retractors and retractor holders such as rings and bars.

2. Description of the Prior Art

In surgery there is a need for clamping devices which hold apparatus, such as retractors and retractor holders, in stable positions in various orientations around the operating field. Retractor arms vary widely in size from ¼" to 1" wide and from ⅛" to ½" thick.

A major consideration in an operating room is maintaining a sterile environment. The more complex the apparatus used in an operating room environment, the more opportunity there is for contamination. Exposed threads on screws and other parts of complex mechanical equipment present contamination hazards as well as posing a hazard of potential parts from a broken piece of equipment falling into the operating field. Exposed components also pose a hazard to the staff in the operating room in terms of bumping into protruding pieces of equipment with a potential of tearing gloves.

Most prior art clamps have exposed threads and other exposed parts which pose the difficulties suggested above.

Some prior art devices provide screw-tightened clamps which rely on the tension of a spring to maintain a tight connection. Springs lose their tension over time, and present an additional sterilization problem as well as a potential hazard of having the spring pop out into the operating field.

DISCLOSURE OF INVENTION

The present invention provides a clamp for surgical apparatus, such as retractors and retractor holders, which can be oriented in a wide variety of orientations by providing a clamp with an integral swivel head at one end, in the form of a ball used with a float and lock ball system.

By providing a completely enclosed clamp with no exposed threads or other interior clamp parts, no blood or biomatter can enter the clamp. This makes cleaning and sterilization no problem and also prevents fouling of the mechanism and prevents any parts from falling out of the clamp.

Providing an interior threaded collar secured to the moving jaw of the clamp eliminates the need for a spring, allowing a longer movement of the gripping jaws and eliminating replacement and tension variation problems with springs.

Providing specially designed jaws allows secure clamping of different sized rectangular devices, enabling the invention to clamp onto any size retractor from ¼" to 1" wide and from ⅛" to ½" thick.

BRIEF DESCRIPTION OF THE DRAWINGS

These and other details and advantages of our invention will be described in connection with the accompanying drawings, which are furnished only by way of illustration and not in limitation of the invention, and in which drawings.

BEST MODE FOR CARRYING OUT THE INVENTION

Figure 1:
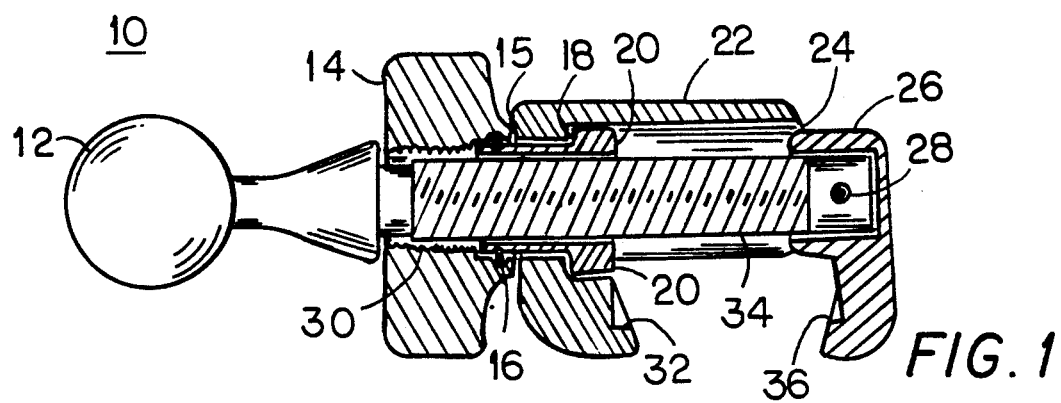
FIG. 1 is a cross-sectional elevation view taken through the longitudinal centerline of the clamp.
Figure 2:
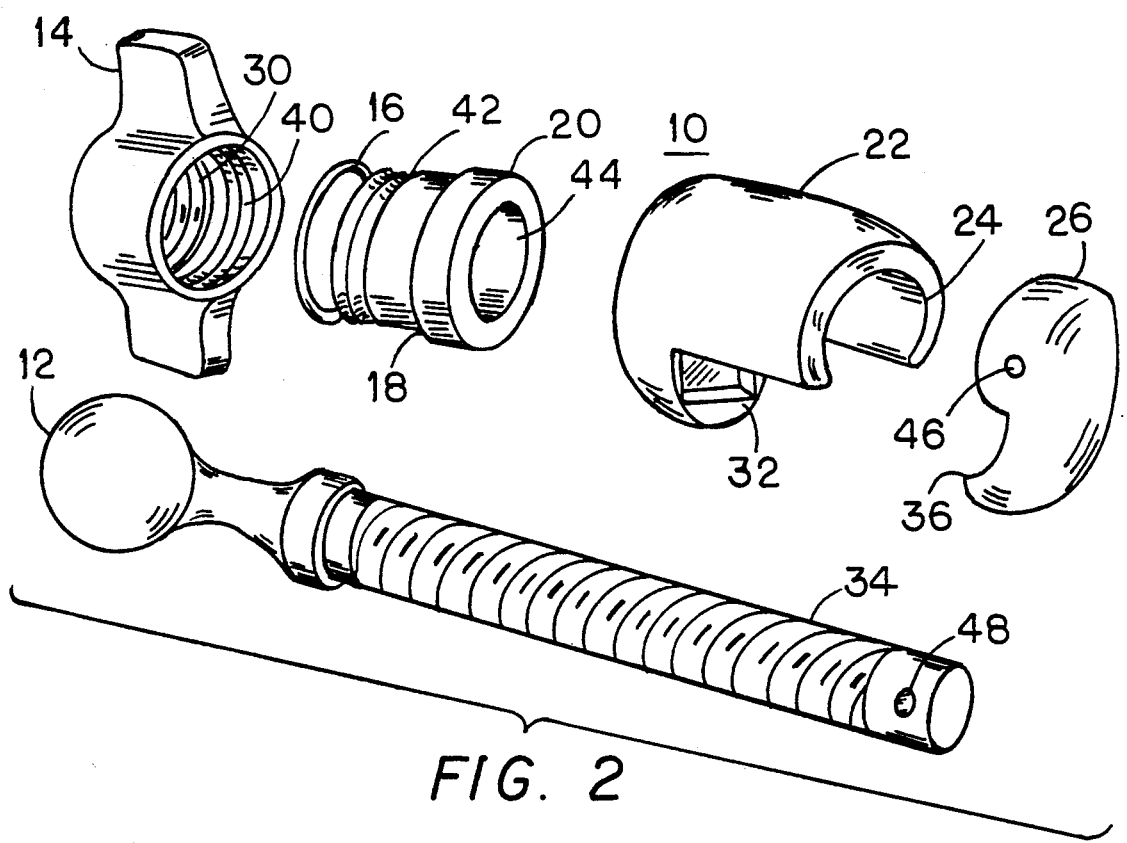
FIG. 2 is an enlarged exploded view showing the components of the clamp.

In FIGS. 1 and 2 an enclosed surgical apparatus clamp 10 comprises a threaded rod 34 secured at one end to a ball 12 or other clamp attaching means. A stationary clamp jaw 36 is fixed to an opposite end of the threaded rod. The stationary clamp jaw comprises an end cap 26 covering the end of the threaded rod with a hooked jaw at the bottom of stationary clamp jaw 36 on an underside of the cap and a pin 28 securing the end cap to the threaded rod through the opening 46 in the side of the end cap.

A movable clamp jaw 32 and cylindrical dome 22 slides along the threaded rod covering both the threaded rod and a portion of the end cap, leaving no interior portion of the threaded rod exposed. The movable clamp jaw comprises a donut-shaped end face 15 encircling the threaded rod with a cylindrical dome 22 extending from a top of the end face over a substantial portion of the threaded rod, over the end cap, and down the sides over the threaded rod to a point even with the jaws. A hooked jaw 32 protrudes from an underside of the end face including a protruding ridge 18.

A turning collar 14 encircles the threaded rod between the movable jaw and the ball. The turning collar comprises interior threads 30 adjacent to the ball end, which threads engage the threads on the threaded rod, finger engaging turning flanges protruding exteriorly, and an interior circular groove 40 adjacent to the movable jaw end.

An interior sleeve 20 encircles the threaded rod connected at one end to the turning collar and engaging the movable jaw end face at another end. The interior sleeve 20 comprises an exterior circular groove 42 at the collar end and a protruding ridge 18 at the jaw end.

A circular ring 16 engages the exterior groove 42 of the sleeve 20 and the interior groove 40 of the turning collar 14 to secure them together. The ridge 18 of the sleeve 20 and the collar 14 sandwich the end face 15 of the movable jaw therebetween linking the movable jaw movement to the movement of the turning collar.

The threaded collar 14 pushes the movable jaw 32 toward the stationary jaw 36 by turning the collar clockwise. The interior sleeve 20 pulls the movable jaw 32 away from the stationary jaw 36 by turning the collar 14 counter-clockwise to release the jaws.

Figure 3:
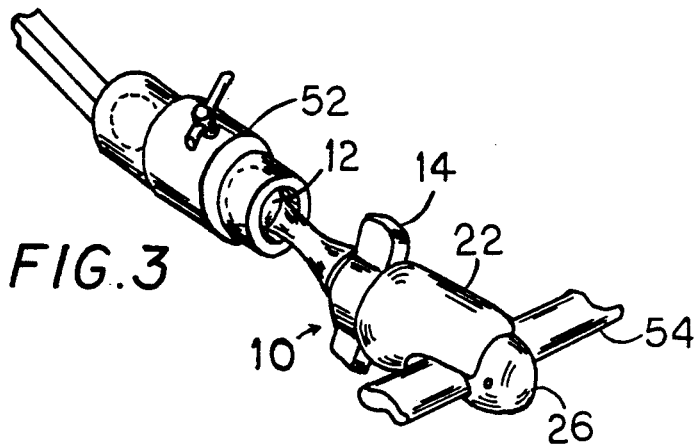
FIG. 3 is a perspective view of the clamp mounted on a float and lock ball system and clamped onto an arm of a retractor.

In FIG. 3 the ball 12 on one end of the clamp is inserted in an existing float and lock ball system 52 attached to a stabilizing post on an operating table bed (not shown). The clamp 10 secures surgical apparatus 54, such as retractors, in place over the patient on the operating table. When the surgical apparatus 54 is gripped by the jaws the clamp is completely enclosed.

All of the components are preferably fabricated from stainless steel or other strong and sterilizable material.

It is understood that the preceding description is given merely by way of illustration and not in limitation of the invention and that various modifications may be made thereto without departing from the spirit of the invention as claimed.

We claim:

1. An enclosed surgical apparatus clamp comprising a threaded rod secured at one end to a clamp attaching means;
   - a stationary clamp jaw and end cap fixed to an opposite end of the threaded rod and covering the end of the threaded rod;
   - a movable clamp jaw and cylindrical dome which slides along the threaded rod, covering both the threaded rod and the end cap;
   - a threaded turning collar encircling and engaging the threaded rod between the movable clamp jaw and a ball;
   - an interior sleeve encircling the threaded rod connected at one end to the turning collar and engaging the movable jaw at another end;
   - wherein the sleeve and the collar sandwich a portion of the movable jaw therebetween linking the movable jaw movement to the movement of the turning collar.

2. The invention of claim 1 wherein the stationary clamp jaw comprises an end cap covering the end of the threaded rod with a hooked jaw on an underside of the end cap.

3. The invention of claim 1 wherein the movable clamp jaw comprises a flat donut-shaped end face encircling the threaded rod with a cylindrical dome extending from a top of the end face over a substantial portion of the threaded rod and over the end cap, and with a hooked jaw protruding from an underside of the end face.

4. The invention of claim 1 wherein the turning collar comprises interior threads adjacent to a ball end, finger engaging turning flanges protruding exteriorly, and an interior circular groove adjacent a movable clamp end.

5. The invention of claim 4 wherein the interior sleeve comprises an exterior circular groove at a collar end and a protruding ridge at a jaw end.

6. The invention of claim 5 further comprising a circular ring engaging the exterior groove of the sleeve and the interior groove of the turning collar to secure them together.

7. The invention of claim 1 wherein the clamp attaching means comprises a ball used with a float and lock ball system.

8. An enclosed surgical apparatus clamp comprising
   - a threaded rod secured at one end to a clamp attaching means;
   - a stationary clamp jaw fixed to an opposite end of the threaded rod, wherein the stationary clamp jaw comprises an end cap covering the end of the threaded rod with a hooked jaw on an underside of the cap;
   - a movable clamp jaw and cylindrical dome which slides along the threaded rod covering both the threaded rod and the cap, wherein the movable clamp jaw comprises a donut-shaped end face encircling the threaded rod with a cylindrical dome extending from a top of the end face over a substantial portion of the threaded rod and over the end cap, and with a hooked jaw protruding from an underside of the end face;
   - a turning collar encircling the threaded rod between the movable clamp and the ball, wherein the turning collar comprises interior threads adjacent to a ball end, which interior threads engage the threaded rod, finger engaging turning flanges protruding exteriorly, and an interior circular groove adjacent a movable clamp end;
   - an interior sleeve encircling the threaded rod connected at one end to the turning collar and engaging the movable jaw end face at another end, wherein the interior sleeve comprises an exterior circular groove at the collar end and a protruding ridge at the jaw end;
   - a circular ring engaging the exterior groove of the sleeve and the interior groove of the turning collar to secure them together;
   - wherein the ridge of the sleeve and the collar sandwich the end face of the movable jaw therebetween linking the movable jaw movement to the movement of the turning collar.

9. The invention of claim 8 wherein the clamp attaching means comprises a ball used with a float and lock ball system.

* * * * *